United States Patent
Savle et al.

(10) Patent No.: US 6,656,936 B1
(45) Date of Patent: Dec. 2, 2003

(54) CARNITINE ANALOGUES AS TOPICAL, MICROBICIDAL SPERMICIDES

(75) Inventors: Prashant S. Savle, West Chester, PA (US); Richard D. Gandour, Blacksburg, VA (US); Gustavo F. Doncel, Norfolk, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 10/049,882
(22) PCT Filed: Aug. 18, 2000
(86) PCT No.: PCT/US00/22615
§ 371 (c)(1), (2), (4) Date: Jul. 5, 2002
(87) PCT Pub. No.: WO01/13920
PCT Pub. Date: Mar. 1, 2001

Related U.S. Application Data

(60) Provisional application No. 60/149,724, filed on Aug. 20, 1999.

(51) Int. Cl.[7] .................... A61K 31/535; C07D 265/30; C07D 265/32
(52) U.S. Cl. .................... 514/230.8; 514/841; 514/843; 514/931; 514/934; 514/944; 514/967; 544/158; 544/173; 564/292
(58) Field of Search .............................. 514/230.8, 841, 514/843, 931, 934, 944, 967; 544/158, 173; 564/292

(56) References Cited

U.S. PATENT DOCUMENTS 5,196,418 A * 3/1993 Gandour et al. ......... 514/230.8

OTHER PUBLICATIONS

Chemical Abstract 118:80881, "Hemipalmitoylcarnitinium strongly inhibits carnitine palmitoyltransferase–1 in intact mitochondria", Gandour et al (1993).*

* cited by examiner

Primary Examiner—Frederick Krass
(74) Attorney, Agent, or Firm—Whitham, Curtis & Christofferson, P.C.

(57) ABSTRACT

Acylcarnitine analogues having alkyl side chains of 10 to 30 carbon atoms display excellent spermicidal and anti-HIV activity, a well as being potent inhibitors of the growth of *Candida albicans*.

47 Claims, 2 Drawing Sheets

CARNITINE ANALOGUES AS TOPICAL, MICROBICIDAL SPERMICIDES

This application is a 371 of PCT/US00/22615, filed Aug. 18, 2000, which claims the benefit of U.S. Provisional Application No. 60/149,724, filed Aug. 20, 1999.

This invention was partially funded from grants from: the National Institutes of Health having grant number GM42016; and the Contraceptive Research and Development (CONRAD) Program, project # CSA98-226, under a cooperative agreement with the United States Agency for International Development (USAID). The government may have certain rights in this invention.

BACKGROUND OF THE INVENTION

1. Field of the Invention

The invention generally relates to novel acylcarnitine analogues and their use as topical, microbicidal spermicides. The acylcarnitine analogues are excellent spermicides, growth inhibitors of *Candida albicans*, and anti-HIV agents.

2. Background of the Invention

Many women want to control their fertility and reduce their risk of becoming infected with a sexually transmitted disease (STD). The AIDS epidemic has intensified the need for female-controlled methods that provide effective protection against both pregnancy and STDs (Irwin et al. 1998). No currently available agent simultaneously protects against both pregnancy and infection. There is a need to develop safe prophylactic agents that are spermicidal and display activity against HIV and STD pathogens.

Nonoxynol-9 (N-9), a nonionic surfactant, is the most widely used spermicides in the United States. Unfortunately, it does not appear to reduce the incidence of HIV infection (Rowe, 1997; Hira et al. 1997; Martin et al., 1997; Roddy et al. 1998). In fact, it has been demonstrated that N-9 actually increases the risk of genital inflammation (Stafford et al., 1998), urinary tract infections (Fihn et al., 1996), vulvovaginal candidiasis (Geiger and Foxman, 1996), and genital ulcers (Feldblum. 1996). One Canadian province no longer recommends the use of N-9 in any form (Rekart, 1992). Furthermore, N-9 is a mixture of oligomers (Yu and Chien, 1995) which may not meet future regulations as the healthcare industry moves toward using pure compounds or mixtures whose individual components have met safety standards. For reasons of environmental toxicity (Thiele et al. 1997), several European nations have banned or restricted the use of N-9 and related compounds, sparking a debate (Renner, 1997) about the health risks of N-9. Clearly, other alternatives to N-9 as a microbicidal spermicide are needed.

It would be of benefit to have available an agent which displayed both spermicidal and anti-STD properties, particularly if the agent was non-irritating and did not increase the risk of inflammation and infection. It would be especially of benefit if the agent was active against the devastating disease of AIDS.

SUMMARY OF THE INVENTION

It is an object of this invention to provide acylcarnitine analogues of the general formula

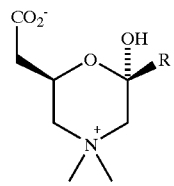

FORMULA 1.

wherein R is an alkyl chain having 10–30 carbons. In the preferred embodiment R is selected from the group consisting of —$C_{10}H_{21}$, —$C_{11}H_{23}$, —$C_{12}H_{25}$, —$C_{13}H_{27}$, —$C_{14}H_{29}$, —$C_{16}H_{33}$, —$C_{17}H_{35}$, —$C_{18}H_{37}$, —$C_{19}H_{39}$, —$C_{20}H_{41}$, —$C_{21}H_{43}$ and —$C_{22}H_{45}$.

It is a further object of the instant invention to provide a composition of matter comprising a carrier and an acylcarnitine analogue of the general formula depicted in Formula 1 wherein R is an alkyl chain selected from the group consisting of —$C_{10}H_{21}$ to —$C_{30}H_{61}$, and where R is preferably —$C_{10}H_{21}$ to —$C_{22}H_{45}$. The composition of matter may further comprise an acid. In a preferred embodiment, the acid is mucic acid. The carrier may be a gel.

The instant invention also provides a method of contraception for a female mammal. In a preferred embodiment, a contraceptively effective amount of a microbicidal spermicide comprising an acylcarnitine analogue as depicted in Formula 1, wherein R is an alkyl chain selected from the group consisting of —$C_{10}H_{21}$ to —$C_{30}H_{61}$, is placed in the vaginal cavity of the female mammal. The microbicidal spermicide may be a gel, and may further comprise an acid such as mucic acid.

The present invention also provides a method of inactivating mammalian spermatozoa, comprising contacting the spermatozoa with a spermicidally effective amount of a compound comprising an acylcarnitine analogue of the general formula depicted in Formula 1, wherein R is an alkyl chain selected from the group consisting of —$C_{10}H_{21}$ to —$C_{30}H_{61}$. In a preferred embodiment, R=—$C_{10}H_{21}$ to —$C_{22}H_{45}$. The compound may be a gel, and may further comprise an acid such as mucic acid.

The present invention also provides a method of neutralizing human immunodeficiency virus, comprising contacting a human immunodeficiency virus with an effective amount of a compound comprising an acylcarnitine analogue of the general formula depicted in Formula 1, wherein R is an alkyl chain selected from the group consisting of —$C_{10}H_{21}$ to —$C_{30}H_{61}$. In a preferred embodiment, R=—$C_{10}H_{21}$ to —$C_{22}H_{45}$. The compound may be a gel, and may further comprise an acid such as mucic acid.

The present invention also provides a method of inhibiting growth of *Candida albicans*, comprising contacting *Candida albicans* with an effective amount of a compound comprising an acylcarnitine analogue of the general formula depicted in Formula 1, wherein R is an alkyl chain selected from the group consisting of —$C_{10}H_{21}$ to —$C_{30}H_{61}$. In a preferred embodiment, R=—$C_{10}H21$ to —$C_{22}H_{45}$. The compound may be a gel, and may further comprise an acid such as mucic acid.

The present invention also provides a method for simultaneously inactivating mammalian spermatozoa, neutralizing human immunodeficiency virus, and inhibiting growth of *Candida albicans* in a female mammal in need thereof, comprising administering intravaginally to a female mammal a quantity of a microbicidal spermicide sufficient to inactivate mammalian spermatozoa, neutralize human immunodeficiency virus, and inhibit growth of *Candida*

*albicans* in said female mammal. The microbicidal spermicide comprises an acylcarnitine analogue of the general formula depicted in Formula 1, wherein R is an alkyl chain selected from the group consisting of —$C_{10}H_{21}$ to —$C_{30}H_{61}$. In a preferred embodiment, R=—$C_{10}H_{21}$ to —$C_{22}H_{45}$. The compound may be a gel, and may further comprise an acid such as mucic acid.

DETAILED DESCRIPTION OF THE PREFERRED EMBODIMENTS OF THE INVENTION

Figure 1:
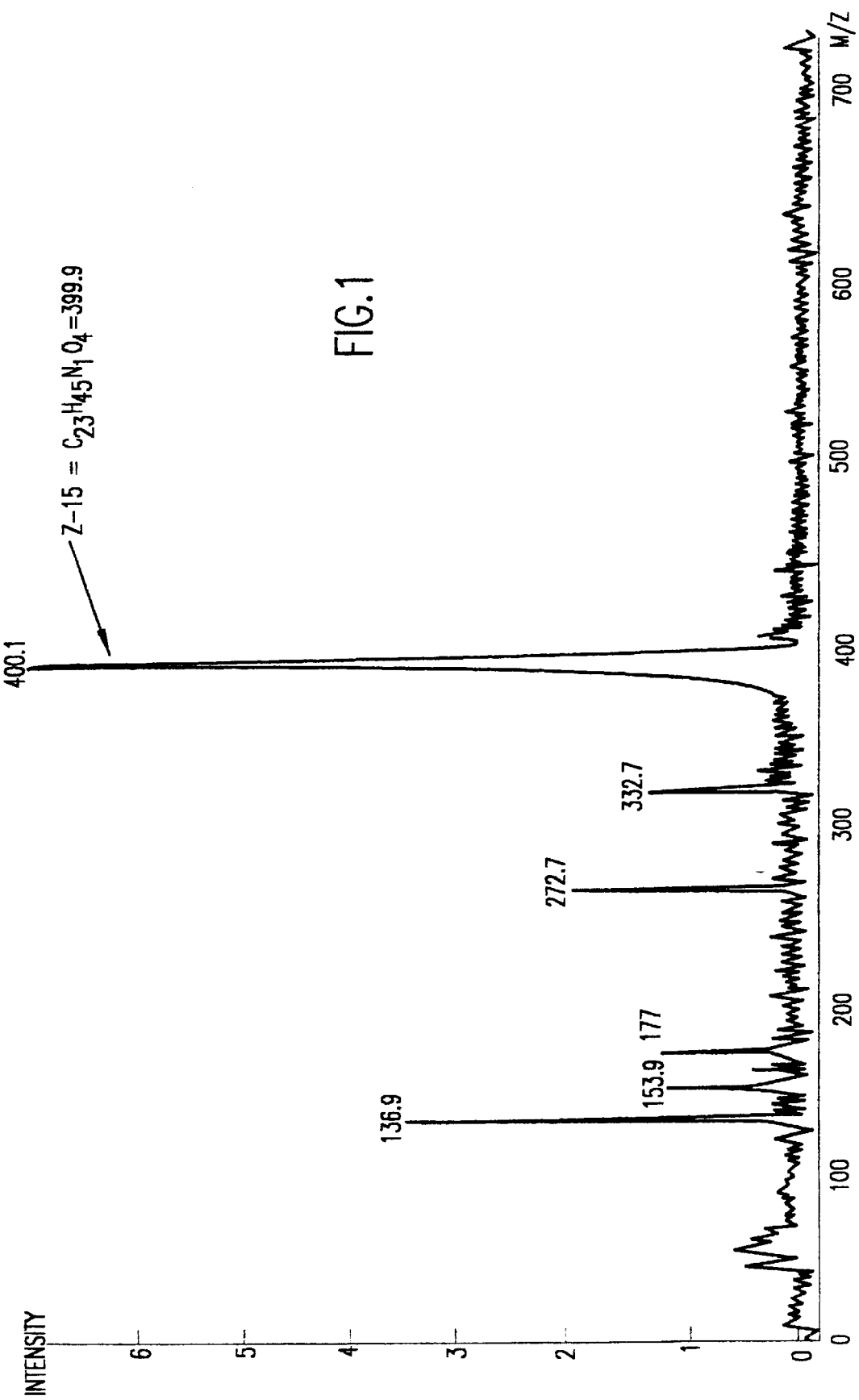
FIG. 1. MALDI-TOF analysis of 4% Z-15 in a carboxymethyl cellulose (CMC) preparation 6 months after Rabbit Vaginal Irritation (RVI) studies.

The present invention provides acylcarnitine analogues which display excellent spermicidal and microbicidal activity. In particular, the analogues are acylcarnitine analogues, and they display excellent activity against HIV, and excellent inhibitory activity against the growth of *Candida albicans*, the fungus that typically causes vaginal yeast infections. Further, the acylcarnitine analogues are non-irritating as demonstrated in standard Rabbit Vaginal Irritation (RVI) studies.

The acylcarnitine analogues are based on the general chemical structure depicted in Formula 1, wherein R=an alkyl chain of from 10 to 30 carbons. Most preferably, R has 10 to 22 carbons (i.e. —$C_{10}H_{21}$ to —$C_{22}H_{45}$). Synthesis of the acylcarnitine analogues is described in Example 1 below. By choosing either the R or S, (or both), stereoisomers of the starting material (noracylcarnitine methyl ester) it is possible to produce the acylcarnitine analogues in either the R or S enantiomeric form, or to produce a racemic mixture of the acylcarnitine analogues. The term "acylcarnitine analogue" is meant to include both R and S stereoisomers, as well as racemic mixtures of stereoisomers.

In one embodiment, the invention provides acylcarnitine analogues of the general formula depicted in Formula 1, where R=an alkyl chain of from 10 to 14 carbons (i.e. —$C_{10}H_{21}$ to —$C_{14}H_{29}$) or from 16 to 22 carbons (i.e. —$C_{14}H_{29}$ to —$C_{22}H_{45}$). The compound in which R=—$C_{15}H_{31}$ has been described previously as a potential diabetes drug.

In another preferred embodiment, the present invention further provides a composition of matter which comprises a carrier and an acylcarnitine analogue of the general formula depicted in Formula 1, wherein R=an alkyl chain of from 10 to 30 carbons, and most preferably 10–22 carbons (i.e. —$C_{10}H_{21}$ to —$C_{22}H_{45}$). In yet another embodiment, the composition of matter may be a gel.

The acylcarnitine analogues have been shown to possess excellent activity against HIV. However, those of skill in the art will recognize that use of the acylcarnitine analogues need not be limited to neutralizing HIV. Other viruses (such as herpes simplex virus) may also be neutralized by the practice of the present invention.

The composition of matter of the present invention may further comprise an acid. Suitable acids would be those which may: increase the water solubility of the analogues; be compatible with vaginal flora (e.g. they may have a buffering capacity which maintains the formulation at a pH of about 4–6); they may help the growth of lactobacilli; they may have preserving qualities and thus augment the potency of the analogues; salts of the acids may be helpful in increasing the crosslinking of carboxymethyl cellulose (CMC) they would be non-toxic and non-irritating. Examples of suitable acids may include but are not limited to citric acid, tartaric acid, lactic acid, malic acid, ascorbic acid (sodium salt), pantothenic acid (sodium salt), lactic acid (sodium salt), various amino acids, mucic acid and the like. In a preferred embodiment of the present invention, the acid is mucic acid.

The acylcarnitine analogue is present in the composition of matter of the present invention in the range of about 1–99% by weight. In a preferred embodiment of the present invention, the acylcarnitine analogue is present in the range of about 2–10% by weight. When mucic acid is present in the composition of matter of the present invention, it is present in the range of about 1–99% by weight. In a preferred embodiment of the present invention, the mucic acid is present in the range of about 1–10% by weight.

The acylcarnitine analogue may be dissolved or dispersed in a number of carriers. For example, it may be formulated for "stand alone" usage in forms which include but are not limited to gels, foams, suppositories, creams, lotions, tablets, pessaries, and the like. Many suitable carriers exist which are well-known to those of skill in the art and which may be used in the practice of the present invention. The use of all such carriers is meant to be encompassed by the present invention. In a preferred embodiment, the carrier is 3% carboxymethyl cellulose (CMC) in $H_2O$. Any formulation which allows the delivery of the acylcarnitine analogue in a quantity sufficient to inactivate spermatozoa, neutralize HIV, and inhibit the growth of *Candida albicans* may be utilized in the practice of the present invention.

The formulations may further include other ingredients which are well-known to those of skill in the art, including but not limited to stabilizers, colorants, preservatives, perfumes, gelling agents, antioxidants, other active ingredients, and the like. The composition of matter of the present invention may contain one or a plurality of acylcarnitine analogues. The acylcarnitine analogues may be of the same or of different alkyl chain lengths, and may be the same or different isomers (R and/or S), or a racemic mixture of isomers, in a single formulation.

The composition of matter of the present invention may also be used in conjunction with other contraceptive devices. Examples include but are not limited to: addition to condoms or diaphragms to enhance their activity, or to imbibe a cervico-vaginal sponge that would act as both a mechanical and chemical barrier against sperm and microbes.

In another embodiment, the present invention also provides a method of contraception in female mammals which involves placing a contraceptively effective amount of a compound of the general formula depicted in Formula 1 in the vaginal cavity of a female mammal. Those of skill in the art will recognize that a variety of means are known by which a compound may be delivered intravaginally, for example plunger-type applicators, pessaries, sprays, squeezeable tubes, cervical rings, sponges, and the like. All such means for intravaginal delivery are intended to be encompassed by the present invention.

The present invention also provides a method of inactivating mammalian spermatozoa which comprises contacting said spermatozoa with spermicidally effective amount of a compound of the general formula depicted in Formula 1.

The present invention also provides a method of neutralizing viruses which comprises contacting viruses with a quantity of a compound of the general formula depicted in Formula 1 sufficient to neutralize the virus. In a preferred embodiment of the present invention, the virus is human immunodeficiency virus. In another preferred embodiment of the present invention, the virus is herpes simplex virus.

The present invention also provides a method of inhibiting the growth of fungi which comprises contacting a fungus with a quantity of a compound of the general formula depicted in Formula 1 sufficient to inhibit the growth of the fungus. In a preferred embodiment of the present invention, the fungus is *Candida albicans*.

The present invention also provides a method of inhibiting the growth of a microbe which comprises contacting the microbe with a quantity of a compound of the general formula depicted in Formula 1 sufficient to inhibit the growth of the microbe. Examples of microbes whose growth may be inhibited by the method of the present invention include but are not limited to viruses, bacteria, protozoa, fungi and parasites.

In other embodiments of the present invention, carnitine alalogues may be utilized as microbicidal agents in commodities other than spermicides. They are especially suited for products intended for topical application because they are non-irritating. For example, they may be added to cosmetic preparations and other hygenic products which include but are not limited to mouthwashes, deodorants, creams, lotions, cosmetics, and the like in order to, for example, effect disinfection, sterilization, or preservation of the product.

In other embodiments of the present invention, the acylcarnitine analogues may be utilized for their intravaginal microbicidal properties alone, i.e. in situations where their spermicidal effects are superfluous. For example, acylcarnitine analogues may be utilized for women who are sterile (e.g surgically sterile, post-menopausal, etc.) or who are utilizing a different form of birth control (e.g. hormonal, intrauterine device, diaphragm, and the like), but who may benefit from the intravaginal microbicidal properties of the compounds. For these purposes, the acylcamitine analogues may be formulated in any of a variety of ways which are well-known to those of skill in the art. Examples include but are not limited to vaginal douches, gels, creams, suppositories, and the like.

EXAMPLES

Example 1

Synthesis

Demethylation of (R)-acylcarnitine by thiophenol in 2-(dimethylamino)ethanol (Colucci et al, 1987) followed by precipitation with LiOH gave 1 in 89% yield. (Refer to Scheme 1 below.) The esterification was modified (Gandour et al, 1993) to improve the yield of 2. Bromohydroxylation of a series of 1-alkenes, followed by in situ oxidation of the resulting secondary alcohol to a ketone by Jones' reagent, gave 3 in good yields. Our previous synthesis (Kumaravel et al, 1993), a minor modification of Zav'yalov et al.'s procedure (Zav'yalov et al., 1989), used acetone as a solvent and gave yields of 3 in the range of 30–55%. However, bromoacetone, a by-product and strong lachrymator, made the workup tedious. The procedure with tetrahydrofuran (THF) eliminated this difficulty. After systematic variation of solvent and alkene, the reaction proceeded reliably in THF/H$_2$O/alkene [(12:12:1)(v/v/w)] as follows:

Synthesis of 1-bromo-2-alkanones, 3. To a solution of 1-alkene (20 mmol) in THF:H$_2$O (1:1, 24 mL/g of alkene), N-bromosuccinimide (NBS) (24 mmol, 1.2 equiv) and FeCl$_3$6H$_2$O (50 mg) were added. The resulting orange solution was stirred until all NBS dissolved (ca. 4–5 hrs). To this solution, Jones' reagent [CrO$_3$(6.1 g, 61 mmol) and conc. H$_2$SO$_4$ (6 mL)] was added while cooling the reaction flask. The dark green reaction mixture was stirred overnight and then diluted with water (50 mL). The reaction mixture was extracted with Et$_2$O (3×30 mL). The ethereal extract was washed with saturated NaHCO$_3$ (2×30 mL), brine (1×20 mL) and dried. Concentration of the extract gave a wax which was chromatographed on silica. Eluting with hexanes followed by 10% Et$_2$O-hexanes gave a colorless waxy solid (yield 70–88%). $^1$H NMR (400 MHz) δ 0.75 (3H, t, J$_{app}$=7.1 Hz), 1.44–1.75 ((n-7)H, br m), 2.65 (2H, t, J$_{app}$=7.1 Hz). 3.89 (2H, s); IR (film) v$_{max}$ 1719.

Condensation (Gandour et al, 1993) of 3 with 2 gave 4. The key to isolating "clean" 4 was triturating the oily residue with EtOAc, then stirring until precipitation occurred. The hydrolysis of 4 with 0.05-N NaOH furnished the desired zwitterions Z-10–Z-15. Multigram quantities of Z-10–Z-15 were separated from NaBr with reverse-phase (RP-8) column chromatography instead of HPLC (Gandour et al, 1993) and, then, recrystallized to yield analytically pure samples. This procedure should also be useful for producing compounds with greater than 15 carbons, e.g. 16 to 30 carbons.

While Z-10–Z-15 compounds were used in the following examples, results with compounds with greater than 15 carbons should be similar.

SCHEME 1.

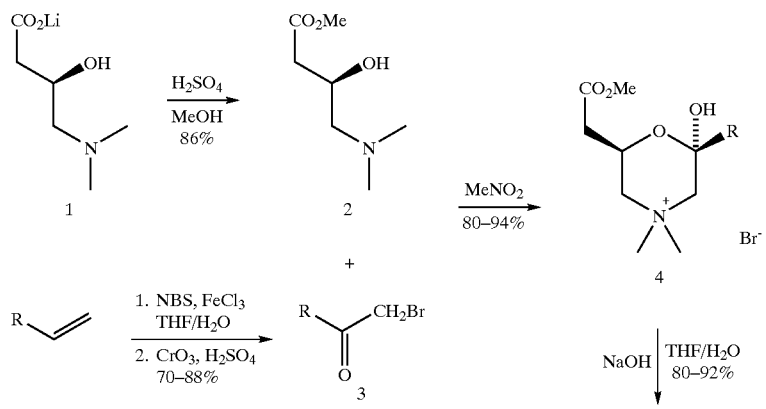

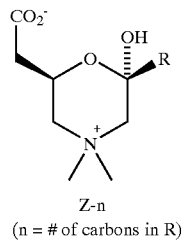

Z-n
(n = # of carbons in R)

Example 2

Spermicidal Activity in the Sander-Cramer Test

Semen samples were collected from healthy human volunteers: only specimens with >60×10$^6$ motile sperm/mL and >50% motility were used. Two-fold serial dilutions of the compounds were prepared in 0.9% saline and incubated with semen samples for 20 seconds. Sperm were assessed under the microscope and positive dilutions (i.e. all observed sperm were immotile) were further incubated at 37° C. for 1 hour with 2 vol. of buffer, and re-examined for sperm motility. If no motile sperm were seen, the positive score was maintained. The Minimum Effective Concentration (MEC) for the compound was calculated using the highest sperm immobilizing dilution and its initial concentration.

Table 1 presents the in vitro assay results for Z-10–Z-15 and N-9. For Z-10–Z-15, the potency increases (i.e. MEC decreases) as the length of the alkyl chain increases until Z-14, the tetradecyl analogue. Within experimental errors. Z-14 and Z-15 have similar MECs; both are slightly lower than that of N-9.

TABLE 1

Spermicidal Activity of Z-10 - Z-15 and N-9 in the Sander-Cramer Test.

| Compound | Solvent | Initial Conc. (mg/ml) | Highest Spermicidal Dilution (1/X) | MEC (mg/mL)$^a$ | n | Solubility |
|---|---|---|---|---|---|---|
| Z-10 | dH$_2$O | 10 | 4.8 ± 0.5 | 2.3 ± 0.2 | 10 | OK |
| (R)-Z-11 | dH$_2$O | 10 | 7.6 ± 0.0 | 1.4 ± 0.1 | 10 | OK |
| (R)-Z-12 | dH$_2$O | 10 | 27.2 ± 2.3 | 0.407 ± 0.7 | 10 | OK |
| (R)-Z-13 | dH$_2$O | 10 | 48.0 ± 5.1 | 0.235 ± 0.025 | 10 | OK |
| (R)-Z-14 | dH$_2$O | 10 | 102.4 ± 18.5 | 0.121 ± 0.014 | 10 | OK |
| (R)-Z-15 | dH$_2$O | 10 | 102.4 ± 9.9 | 0.109 ± 0.012 | 10 | OK |
| N-9 | dH$_2$O | 10 | 83.2 ± 18.2 | 0.144 ± 0.011 | 10 | OK |

$^a$Minimum Effective Concentration

These results show that the acylcarnitine analogues are effective as a spermicide. The test used is an accepted procedure for judging the effectiveness of spermicides (Sander and Cramer, 1941; Doncel, 1994). In use as a spermicide, the acylcamitine analogues would be provided topically to the vagina in a gel, ointment, or other dosage form such that subsequent contact with sperm will result in immobility of the sperm.

Example 3

Inhibition of Candida albicans

The Minimum Inhibitory Concentrations (MICs) of Z-10–Z-15 were measured by determining the inhibition of growth of C. albicans in a solution of mineral salts plus yeast extract (See Standard Practice for Determining Resistance of Synthetic Polymeric Material to Fungi. American Society for Testing and Materials (ASTM) Standards on Materials and Environmental Microbiology, 1$^{st}$ Ed., 1987), and amended with glucose (10 g/L) and yeast extract (1 g/L). An aliquot (250 µl) of sterile medium was dispensed into each well of a 96-well microplate. Stock solutions were prepared by dissolving test compounds in 50% (v/v) aqueous dimethylsulfoxide (DMSO). Each well (plus controls) was then inoculated with 5 µl of a suspension of C. albicans. The suspension was then adjusted to provide OD$_{686}$=0.28. This density contains ca. 2.5×10$^7$ colony forming units (CFU)$^2$/mL. The microplates were incubated in the dark for 4 days at 28° C. Test wells with an OD≦0.05 were judged to exhibit complete inhibition of cellular growth.

The results showed that the Minimum Inhibitory Concentration (MIC) for C. albicans decreases as the chain length increases. The MICs (in mg/mL) are:

| Compound | MIC |
|---|---|
| Z-10 | >0.1 |
| Z-11 | >0.1 |
| Z-12 | 0.08–0.1 |
| Z-13 | 0.04 |
| Z-14 | 0.01 |
| Z-15 | 0.002 |

As can be seen, compound Z-15 displayed the highest activity, and Z-14 displayed acceptable activity.

These results show that the acylcarnitine analogues are effective as inhibitors of the growth of C. albicans. The tests used are accepted procedures for judging the effectiveness of compounds as inhibitors of the growth of C. albicans. In use as a spermicide, the acylcarnitine analogues wound be provided topically to the vagina in a gel, ointment, or other form such that subsequent contact with C. albicans will result in inhibition of growth of C. albicans.

Example 4

Anti-HIV Activity

The assay for in vitro anti-HIV activity followed the previously described procedure (Resnick et al., 1990). An infectious suspension of HIV-1 (RF strain, NIH 1983) was exposed to the compounds for 2 minutes. Immediately after, the mixture was 10-fold serially diluted with medium to terminate compound effect, and the dilutions were incubated with MT-2 target cells at 37° C. The cells were maintained in growth medium at 37° C. for 6 days. HIV-induced cytopathology (syncytium formation) was assessed on day 6 after infection, as was cell viability.

Table 2 presents the results of Z-10–Z-15 and N-9 (control) in in vitro assays for inhibition of cell-free HIV-1 (RF strain). As in the other assays, the effective concentration of antiviral agent decreases as the length of the alkyl chain increases. Within experimental errors. Z-13, Z-14, and Z-15 have similar activities; N-9 is slightly more active than these compounds.

TABLE 2

In Vitro Assay for Inhibition of HIV: Cell-free Inactivation Assay. The effect of the concentration on the reduction of virus activity.

| Compound | Concentration (mg/mL) | | | | | |
|---|---|---|---|---|---|---|
| | 10 | 3.2 | 1 | 0.32 | 0.1 | 0.032 |
| Z-10 | ≧4.0[a] | 2.8 | 1.0 | 0.8 | n.a.[b] | n.a. |
| Z-11 | 4.7 | 2.7 | 2.0 | 0.8 | n.a. | n.a. |
| Z-12 | ≧4.0 | ≧3.5 | 2.8 | 2.0 | 0.3 | 0.0 |
| Z-13 | 3.5 | 3.5 | 3.3 | 2.7 | 1.5 | 0.5 |
| Z-14 | ≧4.0 | ≧4.0 | 3.5 | 2.8 | 1.5 | 0.5 |
| Z-15 | ≧4.0 | 3.8 | 3.2 | 2.7 | 1.5 | 0.3 |
| N-9 | n.a. | n.a. | ≧4.0 | 3.5 | 2.2 | 0.5 |

[a]In log units, values indicate reduction of infective viral titer;
[b]Not assayed These results show that the acylcarnitine analogues are effective as HIV neutralizing agents. The tests used are accepted procedures for judging the effectiveness of compounds as HIV neutralizing agents (Resnick et al. 1990). In use as a microbicide, the acylcarnitine analogues would be provided topically to the vagina in a gel, ointment, or other dosage form such that subsequent contact with HIV will neutralize the virus.

Example 5

Rabbit Vaginal Irritation (RVI) Study

The Food and Drug Administration recommends that all vaginal products be tested in the 10-day RVI (Eckstein et al., 1969) assay prior to clinical trials in women. Table 3 shows a comparison of 4% Z-15 formulated in 3% carboxymethyl cellulose (CMC) in water, 3% CMC in water (vehicle), and two commercial products that are formulations of N-9 in CMC. The results show that the 4% Z-15 in 3% CMC is minimally irritating. The score of 2.7 for the 4% Z-15 formulation is outstanding compared to the commercial products.

TABLE 3

Rabbit vaginal irritation study

| Sample | Score[a] |
|---|---|
| Saline | 3.0 |
| Conceptrol ® (4% N-9) | 7.6 |
| Gynol ® (2% N-9) | 8.2 |
| 4% Z-15 in 3% CMC | 2.7 |
| 3% CMC | 4.4 |

[a]Mean composite score of multiple vaginal tissue samples

Example 6

Effect of Time in Formulation on Activity and Chemical Integrity of Z-15

The spermicidal activity of Z-15 was assayed after three months in the CMC formulations; the results showed that Z-15 was still active as a spermicide after three months.

Residual samples of (R)-Z-15 in the CMC formulation were analyzed with $^1$H nuclear magnetic resonance (NMR) and Matrix Assisted Laser Desorption Ionization Time of Flight Mass Spectroscopy (MALDI-TOF). For the NMR analyses, samples of the hydrogel were dissolved in $D_2O$. For the MALDI-TOF analysis a sample of the hydrogel was placed in the chamber and subjected to the laser. The MALDI-TOF results are depicted in FIG. 1. Both techniques unambiguously showed that Z-15 remained unchanged chemically in the formulations after six months.

Example 7

Cervical Mucus Biodiffusion

The cervical mucus Biodiffusion properties of (R)Z-14 and (R)-Z-15 analogues were tested in comparison to that of N-9 using the Double-End test (Doncel. 1994). In this test, compound solutions (in 0.9% saline) were incubated for 60 minutes with a 7 cm capillary tube containing bovine cervical mucus (Penetrak®, Biochem Immuno System, Norwell, Mass.) opened at one end. After such incubation, the tubes' open end, which had been in contact with the compound, was sealed. Subsequently, the tubes were cut open at 20 mm from the initial opening, inverted, and immersed in semen so as to allow sperm penetration in an opposite direction to that of the compound diffusion. Sperm cease penetration when they encounter a bioactive concentration of the test compound. Thus, the lower the sperm penetration, the greater the compound's biodiffusion. In addition, the spermicidal activity of the analogues was tested again. The results are given in Table 4. As can be seen, the acylcarnitine analogues exhibit similar biodiffusion to N-9 as evidenced by their DET values.

TABLE 4

Cervical mucus biodiffusion

| Compound | Solvent | MEC[a] (mg/ml) | Testing Concentration[b] (mg/mL) | DET[c] % control | n |
|---|---|---|---|---|---|
| (R)-Z-14 | $dH_2O$ | 0.091 ± 0.008 | 0.91 | 18.0 ± 1.2 | −12 |
| (R)-Z-15 | $dH_2O$ | 0.104 ± 0.011 | 1.04 | 16.0 ± 0.0 | 12 |
| N-9 | $dH_2O$ | 0.144 ± 0.011 | 1.44 | 17.5 ± 0.7 | 12 |
| 0.9% NaCl | $dH_2O$ | | | 100.0 ± 0.0 | 12 |

[a]Minimum Effective Concentration per Sander-Cramer assay;
[b]Ten fold MEC.
[c]Double-End Test (% control represents test sperm penetration as compared to control [solvent] sperm penetration)

Example 8

Spermicidal Activities of (R)-, (S), and Racemic (rac)-Z-15

The FDA requires pharmacological evaluation of all stereoisomers of chiral drug candidates (see the FDAs Policy Statement for the Development of New Stereoisomeric Drugs (May. 1, 1992) at http:www.fda.gov/cder/guidance/stereo.htm). Accordingly, (R)-, (S), and (rac)-Z-15 were evaluated for spermicidal activity. A standard Sander-Cramer assay was performed and the results are given in Table 5. As can be seen, there are no significant differences in the activities of both enantiomers and the racemate. In this assay, (rac)-Z-15 is slightly more active than the two enantiomers and significantly more active than N-9.

TABLE 5

Standard Sander-Cramer Assay for (R)-, (S), and (rac)-Z-15

| Compound | Solvent | Initial Conc. (mg/ml) | Highest Spermicidal Dilution (1/X) | MEC (mg/mL)[a] | n | Solubility |
|---|---|---|---|---|---|---|
| (rac)-Z-15 | dH$_2$O | 10 | 115.2 ± 23.6 | 0.117 ± 0.016 | 10 | OK |
| (R)-Z-15 | dH$_2$O | 10 | 73.6 ± 9.1 | 0.156 ± 0.019 | 10 | OK |
| (S)-Z-15 | dH$_2$O | 10 | 80.0 ± 10.4 | 0.148 ± 0.021 | 10 | OK |
| N-9 | dH$_2$O | 10 | 33.6 ± 3.5 | 0.329 ± 0.035 | 10 | OK |

Example 9

Spermicidal Activity of Z-15 Mucic Acid Blends

The recent disclosure (Fassi, U.S. Pat. No. 5,952.379) of stable, non-hygroscopic salts of L-(-)[(R)-]acylcamitine and alkanoyl L-(-)-[(R)-]acylcarnitines with mucic acid (MA) (2:1) prompted the exploration of the effects of blending MA with Z-15. Blending reduced the pH of a sample of Z-15 from about 9–10 to about 3.5–3.8. The blends contained only 67% Z-15 as an active ingredient compared to pure Z-15 (100%). The results are given in Table 6, which shows that a blend of 33% MA and 67% (rac)-Z-15 is as active as any form of Z-15. Further, these experiments again showed that (rac)Z-15 displays activity equal to that of the R and S enantiomers.

TABLE 6

Spermicidal activity of Z-15 - mucic acid blends.

| Compound | Solvent | Initial Conc. (mg/mL) | Highest Spermicidal Dilution (1/X) | MEC (mg/mL) | n | Solubility |
|---|---|---|---|---|---|---|
| (rac)-Z-15[a] | dH$_2$O | 10 | 108.80 ± 19.20 | 0.113 ± 0.015 | 10 | OK |
| AR-Z-15[b] | dH$_2$O | 10 | 96.00 ± 19.67 | 0.129 ± 0.014 | 10 | OK |
| MA-(rac)-Z-15-[c] | dH$_2$O | 10 | 96.00 ± 13.49 | 0.141 ± 0.030 | 10 | OK |
| N-9 | dH$_2$O | 10 | 73.6 ± 8.4 | 0.156 ± 0.020 | 10 | OK |

[a]Lot 964;
[b]gravimetric mixture (50%(S)- plus 50% (R)-Z-15;
[c]33% MA plus 67% rac-Z-15

Example 10

Sperm Motility Inhibition by Z-15-Mucic Acid Blends

Figure 2:
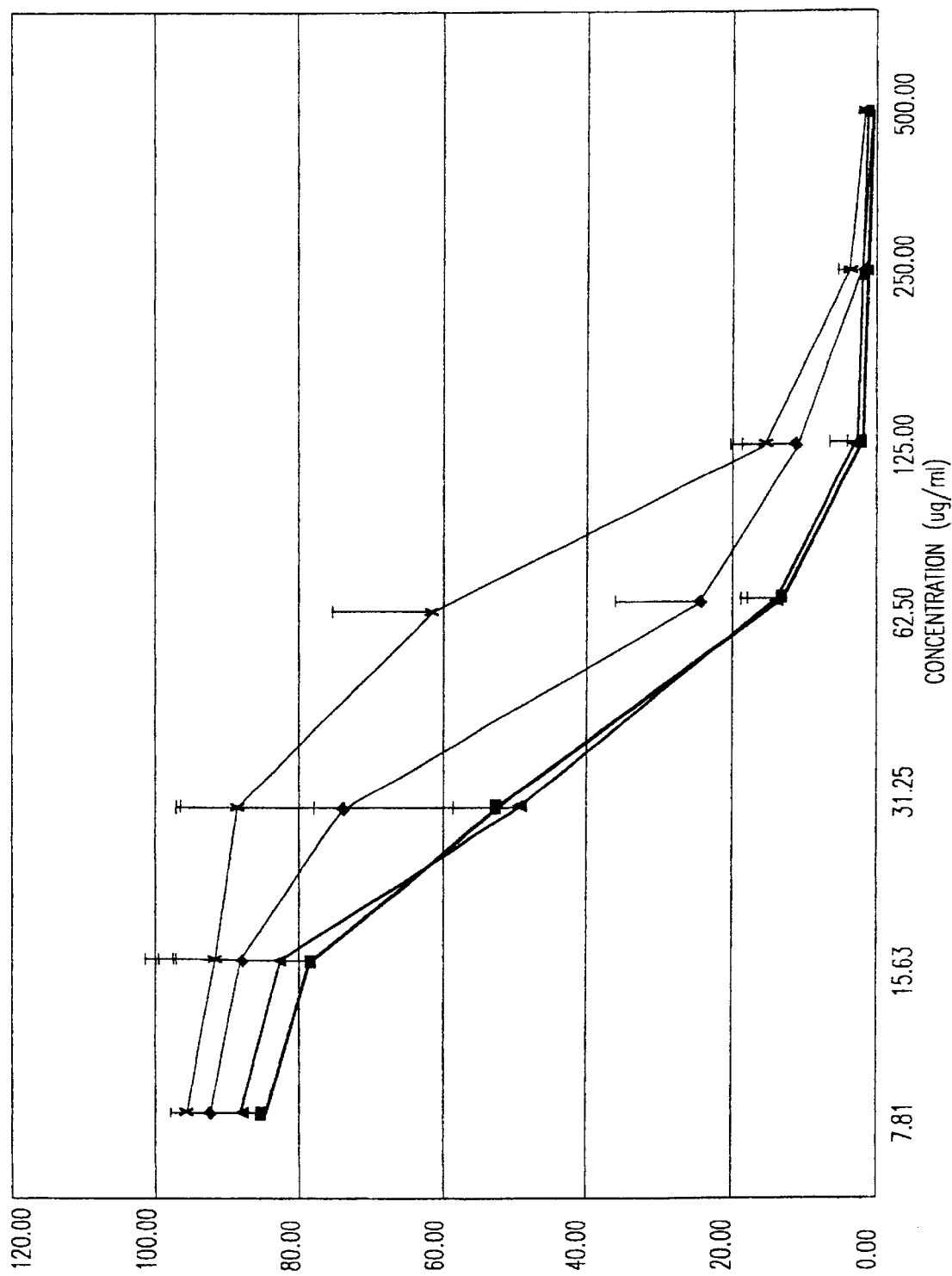
FIG. 2. Z-15 dose-response study: sperm motility assessment. ♦=(R)-Z-15; ■=MA-(rac)-Z-15; ▲=MA-(R)-Z-15; X=N-9.

The ability of Z-15-mucic acid blends [(R)-Z-15-MA and rac-Z-15-MA] to inhibit sperm motility was tested in comparison to (R)-Z-15 alone or N-9. The results are depicted in FIG. 2. As can be seen, both Z-15-mucic acid blends have a lower ED$_{50}$ (Effective Dose 50%, i.e. the dose of the compound that immobilizes 50% of the spermatozoa) than either (R)-Z-15 alone or N-9 alone. Further, these results also demonstrate the superior ability of Z-15 over N-9 to inhibit sperm motility at concentrations below the MEC.

Example 11

Anti-HIV Activity of Formulated Z-15 and a 15-MA Blend

Table 7 contains data demonstrating a dose-dependent inactivation of HIV by a Z-15-MA blend and a gel formulation containing 4% Z-15 in a 3% CMC vehicle.

TABLE 7

Anti-HIV activity of formulated Z-15 and a Z-15-MA blend

| Compound | Solvent | % Agent during Exposure | TCTD$_{50}$ cytotoxicity | log reduction in virus titer[a] |
|---|---|---|---|---|
| MA-(rac)-Z-15-[b] | dH$_2$O | 0.1, 0.032, 0.01, 0.0032 | 15 ≤ 0.5, ≤0.5, ≤0.5 | 3.5, 1.9, 0.7, 0.5 |
| 4% (R)-Z-15 in gel[c] | dH$_2$O | 0.1, 0.032, 0.01, 0.0032 | 1.5, ≤0.5, ≤0.5, ≤0.5 | 3.5, 1.7, ≤0.2, ≤0.2 |
| 3% CMC gel | dH$_2$O | 0.1, 0.032, 0.01, 0.0032 | ≤0.5, ≤0.5, ≤0.5, ≤0.5 | 0.9, ≤0.4, ≤0.2, ≤0.4 |

[a]Virus Control = 6.2-log$_{10}$ TCID$_{50}$/0.1 mL;
[b]33% MA plus 67% rac-Z-15;
[c]Gel consists of 3% CMC in H$_2$O plus 0.18% methylparaben and 0.02% propylparaben.

REFERENCES

Colucci, W. J.; Turnbull, S. P.; Gandour, R. D. *Anal. Biochem.* 1987, 162, 459.

Doncel, G. F. Chemical Vaginal Contraceptives: Preclinical Evaluation in Mauck, C K, Cordero, M, Gabelnick, H. L., Spieler, J. M., Rivera, R. (eds): *Barrier Contraceptives. Current Status and Future Prospects.* Wiley-Liss, Inc. New York, 1994 pp 147–162.

Eckstein, P., Jackson, M. C. N., Sobrero, J. *J. Reprod Fert.* 1969, 20, 85.

Feldblum, P. J. *Genitourin. Med.* 1996, 72, 451.

Fihn, S. D.; Boyko, E. J.; Normand, E. H.; Chen, C.-L.; Grafton, J. R.; Hunt, M.; Yarbro, P.; Scholes, D.; Stergachis, A. *Am. J. Epidemiol.* 1996, 144, 512.

Gandour, R. D.; Leung, O-t; Greway, A. T.; Ramsay, R. R.; Nic a'Bháird. N.; Fronczek, F. R.; Bellard, B. M.; Kumaravel, G. J. *J. Med. Chem.* 1993, 131, 335.

Geiger, A. M.; Foxman. B. *Epidemiology* 1996, 7, 182.

Hira, S. K.,; Feldblum, P. J.,; Kamanga, J.; Mukelabai, G.; Weir, S. S.; Thomas, J. C. *Int. J. STD AIDS* 1997, 8, 243.

Irwin, K; Scarlett, M.; Moseley, R. J. *Women's Health* 1998, 7, 1081.

Kumaravel, G.; Ashendel, C. L.; Gandour, R. D. *J. Med. Chem.* 1993. 36, 177.

Martin. H. L.; Stevens, C. E.; Richardson, B. A.; Rugamba, D.; Nyange. P. M.; Mandaliya, K.; Ndinyaachola, J.; Kreiss, J. K. *Sex. Transm. Dis.* 1997, 24, 279.

Rekart, M. L. *J. Acq. Imm. Def. Syn.* 1992, 5, 425.

Renner, R. *Environ. Sci. Technol.* 1997, 31, A316.

Resnick, L., Busso, M. E., Duncan, C. R. "Anti-HIV Screening Technology" in Alexander, N. J., Gabelnick, H. L., Speiler, J. M. (eds) *Heterosexual Transmission of AIDS.* Wiley-Liss, Inc., New York 1990, pp 311–325.

Roddy, R. E., Zekeng, L.; Ryan, K. A.; Tamoufe, U.; Weir, S. S.; Wong, E. L. *N. Engl. J. Med.* 1998, 339, 504.

Rowe, PIM. *Lancet* 1997, 349, 1074.

Sander, F. V. and Cramer, S. D. *Hum. Fertil.* 1941, 6,134.

Stafford, M. K.; Ward, H.; Flanagan, A.; Rosenstein, I. J.: Taylor-Robinson, D.; Smith, J. R.; Weber, J. and Kitchen, V. S. *J. Acq. Imm. Def. Syn. and Human Retro.* 1998, 4, 327.

Thiele, B.; Guinther, K.; Schwuger, M. J. *Chem. Rev.* 1997, 97, 3247.

Yu, K.; Chien, Y. W. *Int. J. Pharmaceut.* 1995, 125, 81.

Zav'yalov, S. I.; Kravchenko, N. E.; Ezhova, G. I.; Sitkareva, I. V. *Bull. Acad. Sci. USSR, Engl. Transl.* 1989, 2152.

While the invention has been described in terms of its preferred embodiments, those skilled in the art will recognize that the invention can be practiced with modification within the spirit and scope of the appended claims.

We claim:

1. An acylcarnitine analogue of the general formula

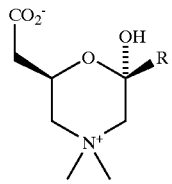

wherein R is an alkyl chain selected from the group consisting of $-C_{10}H_{21}$, $-C_{11}H_{23}$, $-C_{12}H_{25}$, $-C_{13}H_{27}$, $-C_{14}H_{29}$, $-C_{16}H_{33}$, $-C_{17}H_{35}$, $-C_{18}H_{37}$, $-C_{19}H_{39}$, $-C_{20}H_{41}$, $-C_{21}H_{43}$ and $-C_{22}H_{45}$.

2. A composition of matter, comprising, a carrier, and an acylcamitine analogue of the general formula

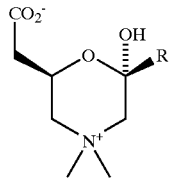

wherein R is an alkyl chain selected from the group consisting of $-C_{10}H_{21}$ to $-C_{30}H_{61}$.

3. The composition of matter of claim 2, further comprising mucic acid.

4. The composition of matter of claim 2 wherein said carrier is a gel.

5. The composition of matter of claim 2 wherein R=$-C_{10}H_{21}$.

6. The composition of matter of claim 2 wherein R=$-C_{11}H_{23}$.

7. The composition of matter of claim 2 wherein R=$-C_{12}H_{25}$.

8. The composition of matter of claim 2 wherein R=$-C_{13}H_{27}$.

9. The composition of matter of claim 2 wherein R=$-C_{14}H_{29}$.

10. The composition of matter of claim 2 wherein R=$-C_{15}H_{31}$.

11. The composition of matter of claim 2 wherein R=$-C_{16}H_{33}$.

12. The composition of matter of claim 2 wherein R=$-C_{17}H_{35}$.

13. The composition of matter of claim 2 wherein R=$-C_{18}H_{37}$.

14. The composition of matter of claim 2 wherein R=$-Cl_{9}H_{39}$.

15. The composition of matter of claim 2 wherein R=$-C_{20}H_{41}$.

16. A method of contraception for a female mammal, comprising placing a contraceptively effective amount of a microbicidal spermicide in a vaginal cavity of said female mammal, said microbicidal spermicide comprising an acylcamitine analogue having the formula

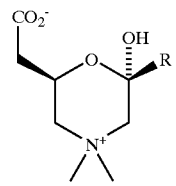

wherein R is an alkyl chain selected from the group consisting of $-C_{10}H_{21}$ to $-C_{30}H_{61}$.

17. The method of claim 16 wherein said microbicidal spermicide is a gel.

18. The method of claim 16 wherein said microbicidal spermicide further comprises mucic acid.

19. The method of claim 16 wherein R=$-C_{10}H_{21}$ to $-C_{22}H_{43}$.

20. A method of inactivating mammalian spermatozoa, comprising contacting said spermatozoa with a spermicidally effective amount of a compound comprising an acylcamitine analogue of the general formula

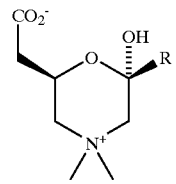

wherein R is an alkyl chain selected from the group consisting of $-C_{10}H_{21}$ to $-C_{30}H_{61}$.

21. The method of claim 20 wherein R=$-C_{10}H_{21}$ to $-C_{22}H_{45}$.

22. The method of claim 20 wherein said compound is a gel.

23. The method of claim 20 wherein said compound further comprises mucic acid.

24. A method of neutralizing a virus, comprising contacting said virus with an effective amount of a compound comprising an acylcarnitine analogue of the general formula

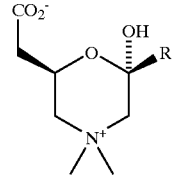

wherein R is an alkyl chain selected from the group consisting of $-C_{10}H_{21}$ to $-C_{30}H_{61}$.

25. The method of claim 24 wherein R=$-C_{10}H_{21}$ to $-C_{22}H_{45}$.

26. The method of claim 24 wherein said compound is a gel.

27. The method of claim 24 wherein said compound further comprises mucic acid.

28. The method of claim 24 wherein said virus is human immunodeficiency virus.

29. The method of claim 24 wherein said virus is herpes simplex virus.

30. A method of inhibiting the growth of a fungus, comprising contacting said fungus with an effective amount of a compound comprising an acylcamitine analogue of the general formula

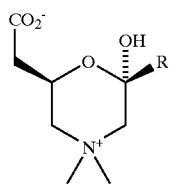

wherein R is an alkyl chain selected from the group consisting of —$C_{10}H_{21}$ to —$C_{30}H_{61}$.

31. The method of claim 30 wherein R=—$C_{10}H_{21}$ to —$C_{22}H_{45}$.

32. The method of claim 30 wherein said compound is a gel.

33. The method of claim 30 wherein said compound further comprises mucic acid.

34. The method of claim 30 wherein said fungus is *Candida albicans*.

35. A method for simultaneously inactivating mammalian spermatozoa, neutralizing human immunodeficiency virus, and inhibiting growth of *Candida albicans* in a female mammal in need thereof, comprising, administering intravaginally to said female mammal a quantity of a microbicidal spermicide sufficient to inactivate mammalian spermatozoa, neutralize human immunodeficiency virus, and inhibit growth of *Candida albicans* in said female mammal, said microbicidal spermicide comprising an acylcarnitine analogue of the general formula

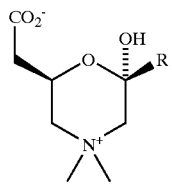

wherein R is an alkyl chain selected from the group consisting of —$C_{10}H_{21}$ to —$C_{30}H_{61}$.

36. The method of claim 35 wherein R=—$C_{10}H_{21}$ to —$C_{22}H_{45}$.

37. The method of claim 35 wherein said microbicidal spermicide is a gel.

38. The method of claim 35 wherein said microbicidal spermicide further comprises mucic acid.

39. A method of inhibiting the growth of a microbe, comprising contacting said microbe with an effective amount of a compound comprising an acylcarnitine analogue of the general formula

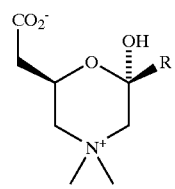

wherein R is an alkyl chain selected from the group consisting of —$C_{10}H_{21}$ to —$C_{30}H_{61}$.

40. The method of claim 39 wherein R=—$C_{10}H_{21}$ to —$C_{22}H_{45}$.

41. The method of claim 39 wherein said compound is a gel.

42. The method of claim 39 wherein said compound further comprises mucic acid.

43. The method of claim 39 wherein said microbe is a virus.

44. The method of claim 39 wherein said microbe is a bacterium.

45. The method of claim 39 wherein said microbe is a protozoa.

46. The method of claim 39 wherein said microbe is a fungus.

47. The method of claim 39 wherein said microbe is a parasite.

* * * * *